US008992766B2

(12) United States Patent
Choudhary et al.

(10) Patent No.: US 8,992,766 B2
(45) Date of Patent: Mar. 31, 2015

(54) METHODOLOGY TO DETERMINE FEED QUALITY (DI+RING AROMATIC CONTENT) OF FCC AND HYDROCRACKING FEEDS

(75) Inventors: Tushar V. Choudhary, Bartlesville, OK (US); Walter E. Alvarez, Bartlesville, OK (US); Joseph E. Bares, Bartlesville, OK (US)

(73) Assignee: Phillips 66 Company, Houston, TX (US)

( * ) Notice: Subject to any disclaimer, the term of this patent is extended or adjusted under 35 U.S.C. 154(b) by 38 days.

(21) Appl. No.: 13/163,204

(22) Filed: Jun. 17, 2011

(65) Prior Publication Data

US 2011/0308996 A1 Dec. 22, 2011

Related U.S. Application Data

(60) Provisional application No. 61/357,140, filed on Jun. 22, 2010.

(51) Int. Cl.
| | |
|---|---|
| *C10G 47/00* | (2006.01) |
| *C10G 11/18* | (2006.01) |
| *C10G 47/36* | (2006.01) |
| *G01N 33/28* | (2006.01) |

(52) U.S. Cl.
CPC .............. *C10G 11/187* (2013.01); *C10G 47/36* (2013.01); *C10G 2300/201* (2013.01); *C10G 2300/301* (2013.01); *C10G 2300/305* (2013.01); *C10G 2300/308* (2013.01); *G01N 33/2823* (2013.01); *C10G 2300/1044* (2013.01); *C10G 2300/1055* (2013.01); *C10G 2400/02* (2013.01); *C10G 2400/04* (2013.01)
USPC ........................................................ 208/108

(58) Field of Classification Search
CPC ................. C10G 11/187; C10G 47/36; C10G 2300/1044; C10G 2400/02; C10G 2400/04; C10G 2300/1055; C10G 2300/305; C10G 2300/308; C10G 2300/301; C10G 2300/201; G01N 33/2823
USPC ........................................................ 208/108
See application file for complete search history.

(56) References Cited

U.S. PATENT DOCUMENTS

| | | |
|---|---|---|
| 2007/0050154 A1 | 3/2007 | Albahri |
| 2007/0212790 A1* | 9/2007 | Welch et al. .................. 436/139 |

OTHER PUBLICATIONS

Tuschar V. Choudhary, Charecterization of heavy petroleum feedstocks, Fuel processing technology 89 (2008), pp. 697-703.*

(Continued)

*Primary Examiner* — Randy Boyer
*Assistant Examiner* — Juan Valencia
(74) *Attorney, Agent, or Firm* — Phillips 66 Company (57) ABSTRACT

A method of upgrading naphtha and diesel yields from fluid catalytic cracking and hydrocracking units by improving a feed quality of a petroleum feedstock, product or fraction mixture. The method of improving the feed quality of the petroleum feedstock, product or fraction mixture occurs by first determining the API Gravity of a petroleum feedstock, product or fraction mixture. A temperature at which about fifty percent of the petroleum feedstock, product or fraction boils ($T_{50}$) is then determined. The feed quality for the petroleum feedstock, product or fraction mixture as determined from the API Gravity and the $T_{50}$ for the feedstock, product or fraction mixture is then estimated followed by adjusting the petroleum feedstock, product or fraction mixture to achieve a higher feed quality.

2 Claims, 3 Drawing Sheets

(56) References Cited

OTHER PUBLICATIONS

Standard Test for Density, Relative Density, and API Gravity of Liquids by Digital Densitty Meter, 2009, pp. 1-8.*

L. Zoccolillo, G.P. Cartoni, A.P. Rizzo and M. Ronchetti, "HPLC Determination of the Aromatic Fraction of Gasoline", Chromatographia vol. 23, No. 11, Nov. 1987, pp. 825-828.

Parviz M. Rahimi and Thomas Gentzis, "The Chemistry of Bitumen and Heavy Oil Processing", Chapter 19, pp. 149-186.

M.E. Fitzgerald, J.L. Moirano, H. Morgan and V.A. Cirillo, "Characterization of Gas Oil Stocks: An Integrated Analysis", Abstract, 3 pages.

Sorood Zahedi, Abghari, Jafar, Towfighi, Darian, Ramin, Karimzadeh, and Mohammad Reza Omidkhah, "Determination of Yield Distribution in Olefin Production by Thermal Cracking of Atmospheric Gasoil", Chemical of Engineering Department, Sep. 2007, pp. 681-692.

"AC MDA Analyzer Determines Aromatic Content of Diesel Fuels Using HPLC", Product Brief, 2 pages.

Kevin M. Van Geem, Damien Hudebine, Marie Francoise Reyniers, Francois Wahl, Jan J. Verstraete and Guy B. Martin, "Molecular Reconstruction of Naptha Steam Cracking Feedstocks Based on Commercial Indices", 2006, 5 pages.

Guilia Bozzano, Mario Dente, Marcos Sugaya, and Colin McGreavy, "The Characterization of Residual Hydrocarbon Fractions with Model Compounds Retaining the Essential Information", pp. 653-657.

Evan N. Chen, Jr., Patrice D. Cusatis and Edward J. Popiel, "Validation of Aromatic Ring Distribution in Diesel Fuel Refinery Streams by Supercrital Fluid Chromatography and Mass Spectrometry", Texaco Research and Development, vol. 637, Issue 2, May 1993, Abstract, 2 pages.

* cited by examiner

METHODOLOGY TO DETERMINE FEED QUALITY (DI+RING AROMATIC CONTENT) OF FCC AND HYDROCRACKING FEEDS

CROSS-REFERENCE TO RELATED APPLICATIONS

This application is a non-provisional application which claims the benefit of and priority to U.S. Provisional Application Ser. No. 61/357,140 filed Jun. 22, 2010, entitled "Methodology to Determine Feed Quality (DI+Ring Aromatic Content) of FCC and Hydrocracking Feeds," which is hereby incorporated by reference in its entirety.

STATEMENT REGARDING FEDERALLY SPONSORED RESEARCH OR DEVELOPMENT

None

FIELD OF THE INVENTION

A methodology to upgrade naphtha and diesel yields from fluid catalytic cracking and hydrocracking units.

BACKGROUND OF THE INVENTION

Fluidized catalytic cracking (FCC) and hydrocracking units are the primary conversion units in an oil refinery. The profitability of the refinery depends on the efficient operation of these units to large degree. The feed quality is an important parameter in conversion optimization.

Sophisticated analytical methods (e.g., High Pressure Liquid Chromatography-Heavy Distillate Analyzer) are required to perform a feed quality analysis (Di+Ring Aromatic Content) of FCC and hydrocracking feedstocks. These analyses are generally not performed at most refineries due to the analytical equipment and expertise required. Accordingly, feed samples are sent offsite for such analyses. Due to the time involved, it is not practical to use these offsite analyses for day-to-day unit optimization.

Accordingly, a methodology is needed to upgrade naphtha and diesel yields from fluid catalytic cracking and hydrocracking units by estimating the feed quality (Di+Ring Aromatic Content) from properties that are routinely measured at most refineries. This methodology would enable a practical method of upgrading naphtha and diesel yields from fluid catalytic cracking and hydrocracking units by improving a feed quality of a petroleum feedstock, product or fraction mixture.

SUMMARY OF THE INVENTION

A method of upgrading naphtha and diesel yields from fluid catalytic cracking and hydrocracking units by improving a feed quality of a petroleum feedstock, product or fraction mixture. The method of improving the feed quality of the petroleum feedstock, product or fraction mixture occurs by first determining the API Gravity of a petroleum feedstock, product or fraction mixture. A temperature at which about fifty percent of the petroleum feedstock, product or fraction boils ($T_{50}$) is then determined. The feed quality for the petroleum feedstock, product or fraction mixture as determined from the API Gravity and the $T_{50}$ for the feedstock, product or fraction mixture is then estimated followed by adjusting the petroleum feedstock, product or fraction mixture to achieve a higher feed quality.

In another embodiment the method describes a method of upgrading naphtha and diesel yields from fluid catalytic cracking and hydrocracking units by improving a feed quality of a petroleum feedstock, product or fraction mixture. The method of improving the feed quality of the petroleum feedstock, product or fraction mixture occurs by first determining an API Gravity of the petroleum feedstock, product or fraction mixture. The method then determines a temperature at which about fifty percent of the petroleum feedstock, product or fraction mixture boils ($T_{50}$) followed by estimating a feed quality for the petroleum feedstock, product or fraction mixture as determined from the API Gravity and the $T_{50}$ for the feedstock, product or fraction mixture.

In this embodiment estimating of the feed quality is performed by calculating a first empirical expression of the form:

$$Di\text{+Ring Aromatic Content (\%)} = A*API(°\,API) + B*T_{50}(°\,F.) + C,$$

wherein Di+Ring Aromatic Content is the feed quality (%) of the petroleum feedstock, product or fraction, API is the API Gravity (° API) of the petroleum feedstock, product or fraction mixture, and $T_{50}$ is the temperature (° F.) at which about fifty percent of the petroleum feedstock, product or fraction boils; and wherein A is a first coefficient, B is a second coefficient and C is a third coefficient.

Afterwards a treadline from a data set is plotted wherein the trendline is in the form:

$$Di\text{+Ring Aromatic Content (\%)} = A'*API(°\,API) + B'*T_{50}(°\,F.) + C',$$

wherein A' is a potential first coefficient, B' is a potential second coefficient, and C' is a potential third coefficient; and adjusting one or more coefficients of the first empirical expression to improve the feed quality estimate.

The first empirical expression is then improved by calculating a second empirical expression of the form:

$$\text{Conversion (wt \%)} = D*(Di\text{+Ring Aromatic Content}) (\text{wt \%}) + E,$$

wherein Conversion is the FCC or hydrocracking conversion (wt %) of the petroleum feedstock, product or fraction mixture, and Di+Ring Aromatic Content is the feed quality (wt %) of the petroleum feedstock, product or fraction; and wherein D is a fourth coefficient, and E is a fifth coefficient.

An improved trendline is then plotted from a data set, wherein the improved trendline is in the form:

$$\text{Conversion (wt \%)} = D'*(Di\text{+Ring Aromatic Content}) (\text{wt \%}) + E',$$

wherein D' is a potential fourth coefficient, and E' is a potential fifth coefficient. One or more coefficients are then adjusted in the second empirical expression to improve the conversion estimate.

The petroleum feedstock, product or fraction mixture is then adjusted to achieve a higher feed quality.

In yet another embodiment the method also describes a method to determine feed quality of petroleum feedstocks, products or fraction mixtures comprising determining an API Gravity for a petroleum feedstock, product or fraction mixture; determining a temperature at which about fifty percent of the petroleum feedstock, product or fraction mixture boils ($T_{50}$); and estimating a feed quality for the petroleum feedstock, product or fraction mixture as determined from the API Gravity and the $T_{50}$ for the feedstock, product or fraction. In this embodiment the estimation of the feed quality is performed in a computer-readable medium having thereon a plurality of instructions, wherein the plurality of instructions when executed by a processor cause the processor to calculate using a first empirical expression of the form:

$$Di\text{+Ring Aromatic Content (\%)}=A*API(°\ API)+B*T_{50}(°\ F.)+C,$$

In this embodiment Di+Ring Aromatic Content is the feed quality (%) of the petroleum feedstock, product or fraction mixture, API is the API Gravity (° API) of the petroleum feedstock, product or fraction mixture, and $T_{50}$ is the temperature (° F.) at which about fifty percent of the petroleum feedstock, product or fraction mixture boils; and wherein A is a first coefficient, is a second coefficient and C is a third coefficient. A trendline is then plotted from a data set, wherein the trendline is in the form:

$$Di\text{+Ring Aromatic Content (\%)}=A'*API(°\ API)+B'*T_{50}(°\ F.)+C',$$

wherein A' is a potential first coefficient, B' is a potential second coefficient, and C' is a potential third coefficient. One is also able to adjust one or more coefficients of the first empirical expression to improve the feed quality estimate.

In this embodiment it is also possible to improve upon the first empirical expression by calculating a second empirical expression of the form:

$$\text{Conversion (wt \%)}=D*(Di\text{+Ring Aromatic Content})(\text{wt \%})+E,$$

wherein conversion is the FCC or hydrocracking conversion (wt %) of the petroleum feedstock, product or fraction, and Di+Ring Aromatic Content is the feed quality (wt %) of the petroleum feedstock, product or fraction mixture; and wherein D is a fourth coefficient, and E is a fifth coefficient.

This is followed by plotting an improved trendline from a data set, wherein the improved trendline is in the form:

$$\text{Conversion (wt \%)}=D'*(Di\text{+Ring Aromatic Content})(\text{wt \%})+E',$$

wherein D' is a potential fourth coefficient, and E' is a potential fifth coefficient.

BRIEF DESCRIPTION OF THE DRAWINGS

For a further understanding of the nature and objects of the present inventions, reference should be made to the following detailed disclosure, taken in conjunction with the accompanying drawings, in which like parts are given like reference numerals, and wherein.

DETAILED DESCRIPTION OF PREFERRED EMBODIMENTS OF THE INVENTION

The following detailed description of various embodiments of the present invention references the accompanying drawings, which illustrate specific embodiments in which the invention can be practiced. While the illustrative embodiments of the invention have been described with particularity, it will be understood that various other modifications will be apparent to and can be readily made by those skilled in the art without departing from the spirit and scope of the invention. Accordingly, it is not intended that the scope of the claims appended hereto to be limited to the examples and descriptions set forth herein but rather that the claims be construed as encompassing all the features of patentable novelty which reside in the present invention, including all features which would be treated as equivalents thereof by those skilled in the art to which the invention pertains. Therefore, the scope of the present invention is defined only by the appended claims, along with the full scope of equivalents to which such claims are entitled.

A methodology to estimate feed quality (Di+Ring Aromatic Content) of fluidized catalytic cracking (FCC) and hydrocracking feeds from properties routinely measured at most refineries is presented below. In an embodiment, the method comprises determining a density, relative density (specific gravity) and/or API Gravity for a petroleum feedstock, product or fraction. The density, relative density (specific gravity), and/or API Gravity may be determined using a Density Analyzer and ASTM D-4052. See ASTM Standard D-86, 2009, Standard Test Method for Density, Relative Density, and API Gravity of Liquids by Digital Density Meter, ASTM International, West Conshohocken, Pa., 2009, DOI: 10.1520/D4052-09.

ASTM D-4052 covers the determination of density, relative density (specific gravity), and API Gravity of petroleum distillates and viscous oils that can be handled as liquids at the temperature of test, utilizing either a manual of automated sample injection equipment. The method application is generally restricted to liquids with total vapor pressures below about 100 kPa and viscosities below about 15,000 mm$^2$/s. However, the method may be extended to >100 kPa if it is first ascertained that no bubbles for in the U-shaped tube, oscillating tube, which can adversely affect the density determination.

Alternatively, density, relative density (specific gravity) and/or API Gravity may be measured using a Hydrometer and ASTM D-1298. See ASTM Standard D-1298, 2005, Standard Test Method for Density, Relative Density (Specific Gravity), or API Density of Crude Petroleum and Liquid Products by Hydrometer Method, ASTM International, West Conshohocken, Pa., 2005, DOI: 10.1520/D1298-99R05.

D-1298 is applicable to crude petroleum, petroleum products or mixtures of petroleum and nonpetroleum products normally handled as liquids, and have a Reid vapor pressure of 101.325 kPa or less.

The specific gravity of the petroleum feedstock, product or fraction may be calculated using the following equation:

$$SG=\rho_{oil}/\rho_{H2O}$$

where

SG is the specific gravity of the petroleum feedstock, $\rho_{oil}$ is the density (kg/m$^3$) of the petroleum feedstock, product or fraction, and $\rho_{H2O}$ is the density (kg/m$^3$) of water.

The API Gravity of a petroleum feedstock, product or fraction may be calculated using the following equation:

$$API(°\ API)=141.5/SG-131.5$$

where

API is the API Gravity (° API) of the petroleum feedstock, product or fraction; and SG is the specific gravity of the petroleum feedstock.

In an embodiment, the method comprises determining a temperature at which fifty percent of the petroleum feedstock, product or fraction boils ($T_{50}$). The $T_{50}$ may be measured using a Gas Chromatography-Simulated Distillation Analyzer and ASTM D-2887. See ASTM Standard D-2887, 2008, Standard Test Method for Boiling Range Distribution of Petroleum Fractions by Gas Chromatography, ASTM International, West Conshohocken, Pa., 2008, DOI: 10.1520/D2887-08.

ASTM D-2887 is applicable to petroleum feedstocks, products and fractions having a final boiling point of 538° C. (1000° F.) or lower at atmospheric pressure. Further, this test method is limited to petroleum feedstocks, products and fractions having a boiling range greater than 55.5° C. (100° F.), and having a vapor pressure sufficiently low to permit sampling at ambient temperature.

Importantly, ASTM D-2887 should not be used to analyze gasoline or gasoline components. Gasoline and gasoline components should be analyzed using a Gas Chromatography-Motor Gasoline Analyzer and ASTM D-3710. See ASTM Standard D-3710, 2009, Standard Test Method for Boiling Point Range Distribution of Gasoline and Gasoline Fractions By Gas Chromatography, ASTM International, West Conshohocken, Pa., 2009, DOI: 10.1520/D3710-95R09.

ASTM D-3710 is applicable to petroleum feedstocks, products and fractions with a final boiling point of 260° C. (500° F.) or lower at atmospheric pressure. This test method is designed to measure the entire boiling range of gasoline and gasoline components with either high or low Reid vapor pressure.

In an embodiment, the method comprises estimating a feed quality (Di+Ring Aromatic Content) for the petroleum feedstock, product or fraction. In particular, the feed quality may be estimated using the following first empirical expression:

$$Di\text{+Ring Aromatic Content (wt \%)} = A*API(° API) + B*T_{50}(° F.) + C$$

where
- Di+Ring Aromatic Content is the feed quality (wt %) of the petroleum feedstock, product or fraction,
- API is the API Gravity (° API) of the petroleum feedstock, product or fraction, and
- $T_{50}$ is the temperature (° F.) at which fifty percent of the petroleum feedstock, product or fraction boils, and where
- A is a first coefficient,
- B is a second coefficient, and
- C is a third coefficient.

In an embodiment, the first coefficient A is between about −0.9 to about −1.0, the second coefficient B is between about 0.009 to about 0.01, and the third coefficient C is between about 23.7 to about 23.9. In another embodiment, the first coefficient A is between about −0.93 to about −0.94, the second coefficient B is between about 0.0097 to about 0.0098, and the third coefficient C is between about 23.78 to about 23.79. In a preferred embodiment, the first coefficient A is about −0.934, the second coefficient B is about 0.00975, and third coefficient C is about 23.786.

In an embodiment, the method comprises determining the feed quality of the petroleum feedstock, product or fraction by high pressure liquid chromatography. For example, the feed quality (Di+Ring Aromatic Content) may be measured using a High Pressure Liquid Chromatography-Heavy Distillate Analyzer (HPLC-HDA). See e.g., A. Z. Khan, *Multi-Dimensional HPLC Determination of Aromatic Core Content, Mass Composition and Aliphatic Side Chain Distribution in Hydrocarbon Fractions of Heavy Distillates*, 49(2) PREPR. PAP.-AM. CHEM. SOC., DIV. FUEL CHEM. (2004) 487-91 ("HPLC-HDA Method").

The HPLC-HAD method determines aromatic content, mass and side chain distributions for six liquid fractions in heavy distillates. These liquid fractions include saturates (paraffins and naphthenes), 1- to 4-ring aromatics and polar (higher than 4-ring, and N-, and O-containing heterocyclic compounds). In particular, six liquid fractions include saturates, the 1-ring aromatics, the 2-ring aromatics, the 3-ring aromatics, the 4-ring aromatics and the polar compounds. In particular, the feed quality may be determined using the flowing expression:

$$(Di\text{+Ring Aromatic Content) (wt \%)} = 2 \text{ ring aromatics (wt \%)} + 3 \text{ ring aromatics (wt \%)} + 4 \text{ ring aromatics (wt \%)}$$

where,
- Di+Ring Aromatic Content is the feed quality (wt %) of the petroleum feedstock, product or fraction;
- 2 ring aromatics is the fraction of 2 ring aromatics (wt %) in the petroleum feedstock, product or fraction;
- 3 ring aromatics is the fraction of 3 ring aromatics (wt %) in the petroleum feedstock, product or fraction; and
- 4 ring aromatics is the fraction of 4 ring aromatics (wt %) in the petroleum feedstock, product or fraction.

In an embodiment, the method comprises comparing one or more of the feed quality estimates as determined from the API Gravity and the $T_{50}$ to a corresponding feed quality measurement as determined by high pressure liquid chromatography.

In an embodiment, the method comprises adjusting one or more coefficients of the empirical expression to improve the feed quality estimate. As discussed above, the first coefficient A is between about −0.9 to about −1.0, the second coefficient B is between about 0.009 to about 0.01, and the third coefficient C is between about 23.7 to about 23.9. In another embodiment, the first coefficient A is between about −0.93 to about −0.94, the second coefficient B is between about 0.0097 to about 0.0098, and the third coefficient C is between about 23.78 to about 23.79. In yet another embodiment, the first coefficient A is about −0.934, the second coefficient B is about 0.00975, and third coefficient C is about 23.786. It is important to note that the coefficients will change depending on the process conditions therefore different than those listed above are possible.

However, these coefficients may vary slightly for different petroleum feedstocks, products or fractions. Accordingly, these coefficients may be adjusted to improve the statistical fit of the first empirical expression to plant historical data, and to improve feed quality estimates for plant feedstocks, product or fractions.

In an embodiment, the method comprises using a computer system that is specially-adapted with a data analysis package to adjust a trendline from a data set. The analysis package is commercially available from a number of companies. For example, Microsoft Corporation has the Office Excel® 2007 spreadsheet software that can be used as a data analysis package. In one embodiment, the Microsoft Office Excel® 2010 software is used as the data analysis package.

For example, property data for various petroleum feedstocks, products or fractions including API Gravity, $T_{50}$, and feed quality (Di+Ring Aromatic Content) is shown in Table 1.

TABLE 1

Property Data for Various Petroleum Feedstocks, Products or Fractions Including API Gravity, $T_{50}$ and Feed Quality (Di + Ring Aromatic Content).

| API Gravity (°API)[1] | T50 (° F.)[2] | Feed Quality (Di + Ring Aromatic Content) | |
|---|---|---|---|
| | | Estimated (%) | Experimentally Measured (%)[3] |
| 14.21 | 828.1 | 18.6 | 18.4 |
| 24.44 | 782.2 | 8.6 | 8.4 |
| 25.535 | 769.8 | 7.4 | 9.1 |
| 20.44 | 818.8 | 12.7 | 14.4 |
| 23.59 | 806 | 9.6 | 7.7 |
| 23.93 | 804.9 | 9.3 | 7.2 |
| 24.335 | 800.6 | 8.9 | 7.4 |
| 21.105 | 752.7 | 11.4 | 8.4 |
| 21.235 | 751.6 | 11.3 | 8.9 |
| 21.59 | 746.8 | 10.9 | 9.2 |
| 15 | 801 | 17.6 | 21.0 |
| 21.14 | 772.7 | 11.6 | 11.5 |
| 21.71 | 767.5 | 11.0 | 11.6 |
| 24.95 | 775.3 | 8.0 | 5.1 |
| 22.35 | 761.3 | 10.3 | 11.2 |
| 22.92 | 759.1 | 9.8 | 6.6 |
| 18.85 | 810.4 | 14.1 | 15.3 |
| 22.6 | 803.5 | 10.5 | 10.6 |
| 22.925 | 797.1 | 10.1 | 8.9 |
| 23.33 | 793.2 | 9.7 | 9.9 |
| 15.97 | 848.9 | 17.1 | 19.7 |
| 20.795 | 822 | 12.4 | 11.2 |
| 21.24 | 816.5 | 11.9 | 13.5 |
| 21.79 | 811.2 | 11.3 | 12.9 |
| 18.69 | 808.8 | 14.2 | 12.3 |
| 19.33 | 804.6 | 13.6 | 11.6 |
| 23.6 | 798 | 9.5 | 11.6 |
| 24.8 | 813 | 8.5 | 9.6 |
| 24.5 | 726 | 8.0 | 9.5 |
| 24.2 | 802 | 9.0 | 7.2 |
| 23.8 | 812 | 9.5 | 11.4 |
| 21.7 | 788 | 11.2 | 13.9 |
| 24.6 | 739 | 8.0 | 6.5 |
| 22.9 | 751 | 9.7 | 10.0 |
| 22.6 | 757 | 10.1 | 10.7 |
| 22.2 | 783 | 10.7 | 8.7 |
| 25.2 | 836 | 8.4 | 9.5 |
| 21.4 | 804 | 11.6 | 13.4 |

[1]The API Gravity of the petroleum feedstock, product or fraction was experimentally measured using a Density Analyzer and ASTM D-4052.
[2]The $T_{50}$ of the petroleum feedstock, product or fraction was experimentally measured using a Gas Chromatography - Simulated Distillation Analyzer and ASTM D-2887.
[3]The feed quality (Di + Ring Aromatic Content) of the petroleum feedstock, product or fraction was experimentally measured using a High Pressure Liquid Chromatography - Heavy Distillate Analyzer and HPLC-HDA Method.

In an embodiment, the method comprises estimating the conversion from one or more liquid fractions in the petroleum feedstock, product or fraction. In particular, the FCC or hydrocracking conversion may be estimated using the following second empirical expression:

Conversion (wt %)=$D$*($Di$+Ring Aromatic Content) (wt %)+$E$ where
Conversion is the FCC or hydrocracking conversion (wt %) of the petroleum feedstock, product or fraction, and
Di+Ring Aromatic Content is the feed quality (wt %) of the petroleum feedstock, product of fraction, and
where
D is a fourth coefficient, and
E is a fifth coefficient.

In an embodiment, the fourth coefficient D is between about −2.0 to about −3.5, and the fifth coefficient E is between about 85.0 to about 110.0. In one embodiment, the fourth coefficient D is about −3.252, and the fifth coefficient E is about 104.24. In yet another embodiment, the fourth coefficient D is about −2.2433, and the fifth coefficient E is about 90.787. It is important to note that the coefficients will change depending on the process conditions therefore different than those listed above are possible.

For example, property data for various petroleum feedstocks, products or fractions including feed quality (Di+Ring Aromatic Content) and FCC or hydrocracking conversion is shown in Table 2.

TABLE 2

Property Data for Various Petroleum Feedstocks, Products or Fractions Including Feed Quality (Di + Ring Aromatic Content) and Conversion.

Figure 1:
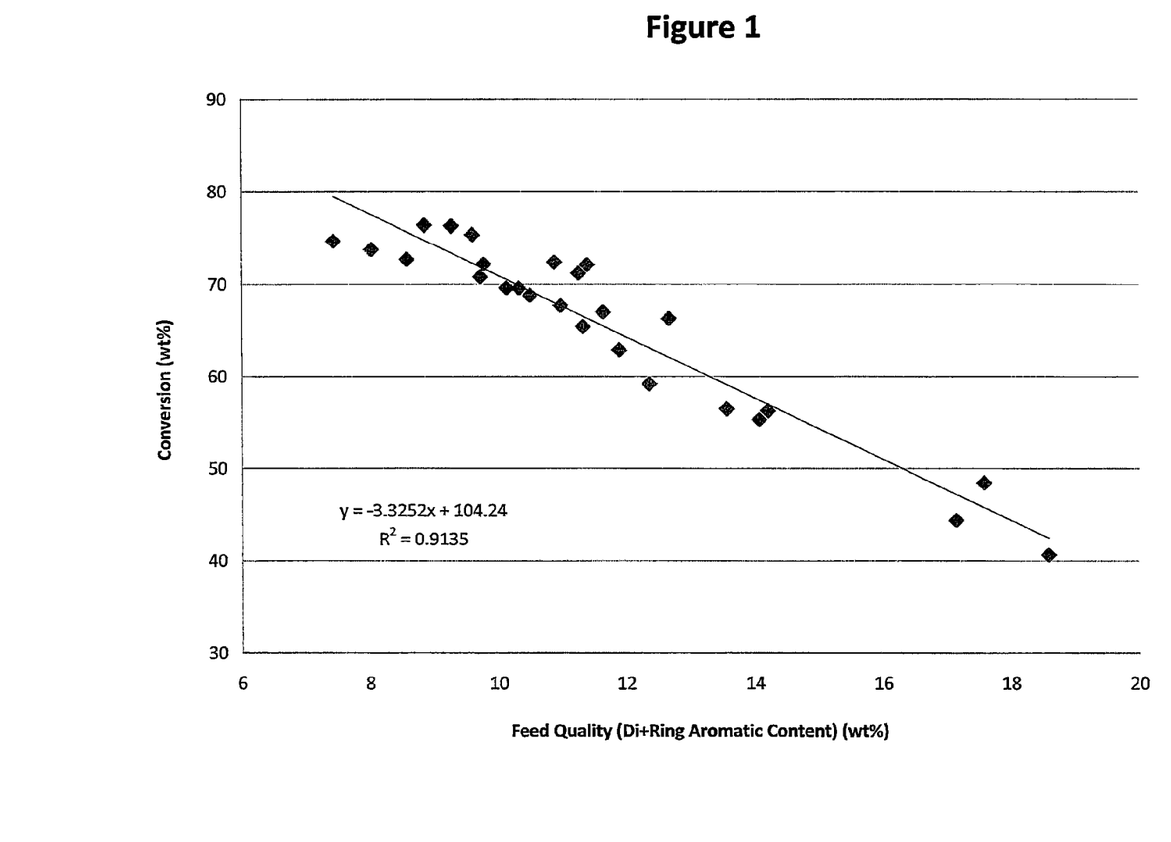
FIG. 1 depicts a plot of FCC conversion (wt %) verses feed quality (Di+Ring Aromatic Content) (wt %), showing a correlation of about $R^2=0.9135$.
Figure 2:
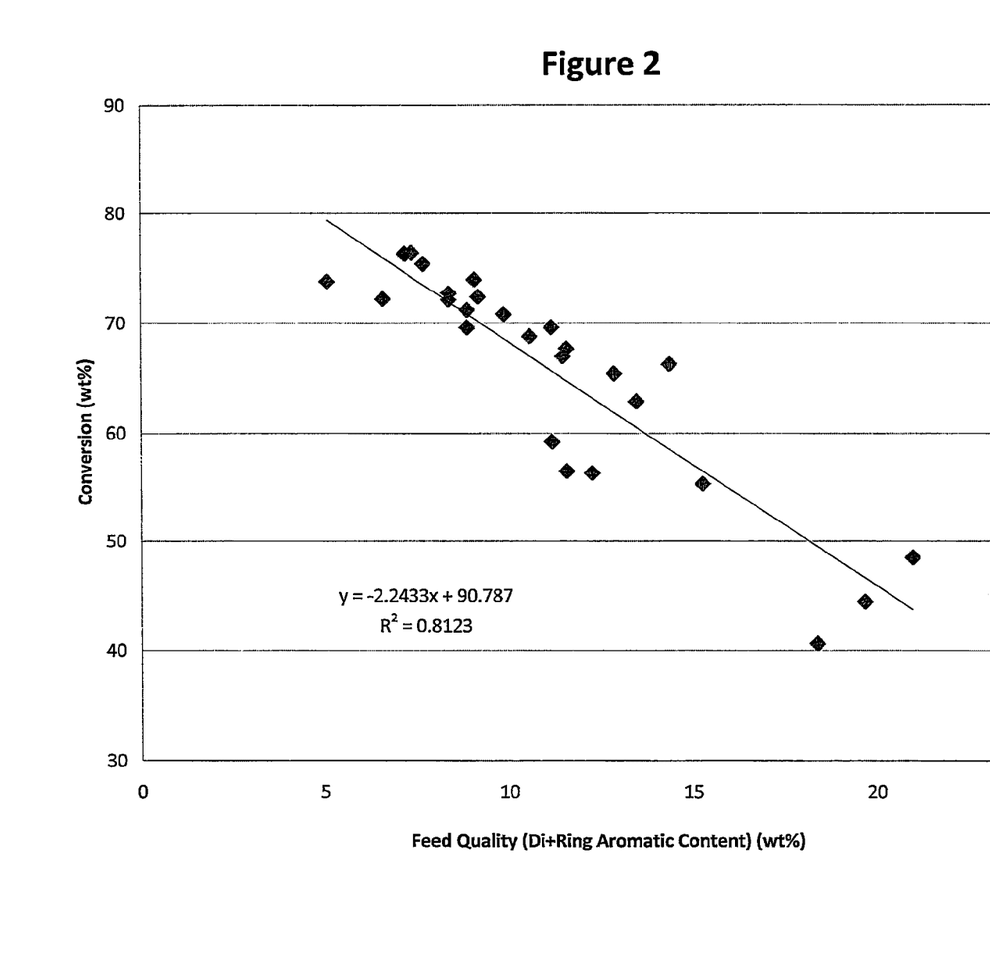
FIG. 2 depicts a plot of FCC conversion (wt %) verses feed quality (Di+Ring Aromatic Content) (wt %), showing a correlation of about $R^2=0.8123$.

| FIG. 1 | | FIG. 2 | |
|---|---|---|---|
| Feed Quality (Di + Ring Aromatic Content) (wt %)[1] | Conversion (wt %)[2] | Feed Quality (Di + Ring Aromatic Content) (wt %)[1] | Conversion (wt %)[2] |
| 18.59 | 40.6 | 21 | 48.5 |
| 17.59 | 48.5 | 19.7 | 44.4 |
| 17.15 | 44.4 | 18.4 | 40.6 |
| 14.21 | 56.3 | 15.3 | 55.3 |
| 14.08 | 55.3 | 14.4 | 66.3 |
| 13.58 | 56.5 | 13.5 | 62.9 |
| 12.68 | 66.3 | 12.9 | 65.4 |
| 12.38 | 59.2 | 12.3 | 56.3 |
| 11.91 | 62.9 | 11.6 | 67.7 |
| 11.66 | 67 | 11.6 | 56.5 |
| 11.41 | 72.1 | 11.5 | 67 |
| 11.34 | 65.4 | 11.2 | 69.6 |
| 11.28 | 71.2 | 11.2 | 59.2 |
| 10.99 | 67.7 | 10.6 | 68.8 |
| 10.90 | 72.4 | 9.9 | 70.8 |
| 10.51 | 68.8 | 9.2 | 72.4 |
| 10.33 | 69.6 | 9.1 | 74 |
| 10.14 | 69.6 | 8.9 | 69.6 |
| 9.78 | 72.2 | 8.9 | 71.2 |
| 9.73 | 70.8 | 8.4 | 72.1 |
| 9.61 | 75.4 | 8.4 | 72.7 |
| 9.28 | 76.3 | 7.7 | 75.4 |
| 8.86 | 76.4 | 7.4 | 76.4 |
| 8.58 | 72.7 | 7.2 | 76.3 |
| 8.03 | 73.8 | 6.6 | 72.2 |
| 7.44 | 74.7 | 5.1 | 73.8 |

[1]The feed quality (Di + Ring Aromatic Content) of the petroleum feedstock, product or fraction was experimentally measured using a High Pressure Liquid Chromatography - Heavy Distillate Analyzer and HPLC-HDA Method.
[2]The conversion of the petroleum feedstock, product or fraction was determined using a Gas Chromatography - Simulated Distillation Analyzer and ASTM D-2887.

As an example, a plot of feed quality (Di+Ring Aromatic Content) (wt %) FCC or hydrocracking conversion (wt %) of a petroleum feedstock, product or fraction, showing a correlation of about $R^2$=0.9135 is shown in FIG. 1. As shown in FIG. 1, the trendline from the data set is in the form:

Conversion (wt %)=$D$*($Di$+Ring Aromatic Quality) (wt %)+$E$, where D is about −3.3252 and E is about 104.24. This trendline has a correlation of about $R^2$=0.9135.

A plot of feed quality (Di+Ring Aromatic Content) (wt %) verses FCC or hydrocracking conversion (wt %) of a petroleum feedstock, product or fraction, showing a correlation of about $R^2$=0.8123 is shown in FIG. 2. As shown in FIG. 1, the trendline from the data set is also in the form:

Conversion (wt %)=$D$*($Di$+Ring Aromatic Quality) (wt %)+$E$, where D is about −2.2433 and E is about 90.787. This trendline has a correlation of about $R^2$=0.8123.

In an embodiment, the method comprises reacting the petroleum feedstock, product or fraction over an equilibrium catalyst as in a simulated or plant process. For example, the petroleum feedstock may be reacted over an equilibrium catalyst in an Advanced Catalyst Evaluation (ACE) unit or, alternatively, in a plant process to obtain a reacted petroleum feedstock, product or fraction. In an embodiment, an equilibrium catalyst is provided by the plant process for simulation in the ACE unit. The catalyst should be calcined under flowing air at a temperature of 1292° F. for a period of 1.5 hours. The conversion reactions may be carried out with Catalyst to Oil (C/O) ratios of 4, 6 and 8, and at a temperature of 985° F.

In an embodiment, the method comprises determining one or more liquid fractions of the reacted petroleum feedstock, product or fraction. In a preferred embodiment, the liquid fractions for light cycle oil and 650° F.+ oil in the reacted petroleum feedstock, product or fraction are determined. The liquid fractions may be determined using a Gas Chromatography-Simulated Distillation Analyzer and ASTM D-2887. See ASTM Standard D-2887, 2008, Standard Test Method for Boiling Range Distribution of Petroleum Fractions by Gas Chromatography, ASTM International, West Conshohocken, Pa., 2008, DOI: 10.1520/D2887-08.

ASTM D-2887 is applicable to petroleum products and fractions having a final boiling point of 538° C. (1000° F.) or lower at atmospheric pressure, as discussed above. Further, this test method is limited to petroleum products and fractions having a boiling range greater than 55.5° C. (100° F.), and having a vapor pressure sufficiently low to permit sampling at ambient temperature.

Importantly, ASTM D-2887 should not be used to analyze gasoline or gasoline components. Gasoline and gasoline components should be analyzed using a Gas Chromatography-Motor Gasoline Analyzer and ASTM D-3710. See ASTM Standard D-3710, 2009, Standard Test Method for Boiling Point Range Distillation of Gasoline and Gasoline Fractions By Gas Chromatography, ASTM International, West Conshohocken, Pa., 2009, DOI: 10.1520/D3710-95R09.

ASTM D-3710 is applicable to petroleum feedstocks, products and fractions with a final boiling point of 260° C. (500° F.) or lower at atmospheric pressure. This test method is designed to measure the entire boiling range of gasoline and gasoline components with either high or low Reid vapor pressure.

Alternatively, the petroleum feedstocks, products and fractions may be analyzed using a Laboratory Batch Distillation Unit and ASTM D-86. See ASTM Standard D-86, 2009, Standard Test Method for Distillation of Petroleum Products at Atmospheric Pressure, ASTM International, West Conshohocken, Pa., 2009, DOI: 10.1520/D0086-09E01.

ASTM D-86 is applicable for the analysis of distillate fuels such as light and middle distillates, automotive spark-ignition fuels, automotive spark-ignition fuels containing up to 10% ethanol, aviation gasoline, aviation turbine fuels, 1-D and 2-D diesel fuels, biodiesel blends up to 20%, marine fuels, special petroleum spirits, naphthas, white spirits, kerosines and Grades 1 and 2 burner fuels. The method is not applicable to products containing appreciable quantities of residual material.

In an embodiment, the method comprises determining the conversion of the petroleum feedstock, product or fraction from one or more liquid fractions of the reacted petroleum feedstock, product or fraction. In particular, the FCC conversion may be determined using the following expression:

$$\text{Conversion (wt \%)} = 100 - FR_{LCO}(\text{wt \%}) - FR_{650° F.+}(\text{wt \%})$$

where
Conversion is the FCC conversion (wt %) of the petroleum feedstock, product or fraction;

$FR_{LCO}$ is the fraction of the light cycle oil (wt %) in the reacted petroleum feedstock, product or fraction; and $FR_{650° F.+}$ is the fraction of the 650° F. (and heavier) oil (wt %) in the reacted petroleum feedstock, product or fraction.

In an embodiment, the method comprises comparing one or more of the conversion estimates as determined from feed quality (Di+Ring Aromatic Content) of the petroleum feedstock, product or fraction to a corresponding conversion measurement as determined from one or more liquid fractions of the reacted petroleum feedstock, product or fraction.

In an embodiment, the method comprises adjusting one or more coefficients of the second empirical expression to improve the conversion estimate. As discussed above, the fourth coefficient D is between about −2.0 to about −3.5, and the fifth coefficient E is between about 85.0 to about 110.0. In a preferred embodiment, the fourth coefficient D is about −3.252, and the fifth coefficient E is about 104.24. In another preferred embodiment, the fourth coefficient D is about −2.2433, and the fifth coefficient E is about 90.787.

However, these coefficients may vary slightly for different petroleum feedstocks, products or fractions. Accordingly, these coefficients may be adjusted to improve the statistical fit of the second empirical expression to plant historical data, and to improve conversion estimates for plant feedstocks, products or fractions. As discussed above, adjusting a trendline from a data set is well known to plant chemists and engineers.

Figure 3:
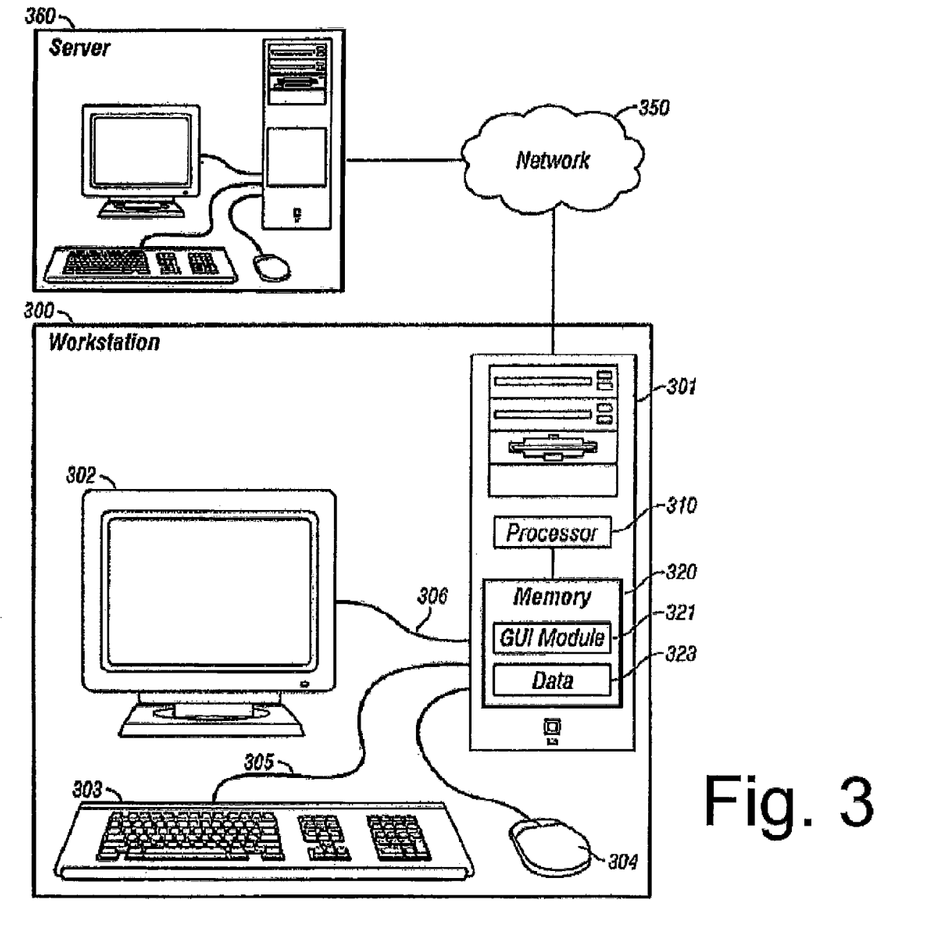
FIG. 3 depicts an illustration of a computer system to perform the embodiments.

FIG. 3 depicts an illustration of a computer system to perform some of the embodiments of this method. A workstation (300) includes a computer (301), which can be coupled to a video display (302) via an external graphics bus (306). The external graphics bus (306) can be an Advanced Graphics Port (AGP) compliant bus. The term "coupled" encompasses a direct connection, an indirect connection, or the like. The computer (301) in one embodiment includes a processor (310), such as the Pentium™ III processor manufactured by Intel Corp. of Santa Clara, Calif. In another embodiment, the processor (310) can be an Application Specific Integrated Circuit (ASIC). The computer (301) can include a memory (320) coupled to the processor. The memory (320) can encompass devices adapted to store digital information, such as Dynamic Random Access Memory (DRAM), Rambus™ DRAM (RDRAM), flash memory, a hard disk, an optical digital storage device, a combination thereof. The computer (301) can be coupled to a keyboard (303) and a mouse (304) via an external computer bus (305). In one embodiment, the external computer bus (305) is a Universal Serial Bus (USB) compliant bus.

The memory (320) can include instructions adapted to be executed by the processor (310) to perform a method in accordance with an embodiment of the present invention. The term "instructions adapted to be executed" is meant to encompass any instructions that are ready to be executed in their present form (for example, machine code) by a processor, or that require further manipulation, for example compilation, decryption, decoding, or provided with an access code, etc., to be ready to be executed by a processor. In one embodiment, the memory (320) can include a graphical user interface (GUI) module (321) to implement an interface.

In an embodiment, the workstation (300) is coupled to a server (360) via a network (350). Examples of network (350) include the internet, a WAN (wide area network), a LAN (local area network), an intranet, a communications network, a computer network, and combinations thereof. In one embodiment, the server (360) is coupled to a storage device that typically stores data on a magnetic medium, such as a magnetic disk. For example, the storage device may store application programs and associated data files/documents. Examples of documents include word processing documents, spreadsheet documents, HTML (Hypertext Markup Language) documents, and the like. Workstation (300) can access data stored in the storage device via server (360) and network (350). In an embodiment, server (360) can display information on display (302) by sending information signals to workstation (300) via network (350). Examples of display information include data, a GUI component, a web page, and the like.

Data (323) can encompass hierarchical data, non-hierarchical data, and the like. Data (323) can be a document corresponding to a particular application, such as a word processing document, a spreadsheet document, an HTML document, and the like. Further, the data can be digital data, analog data, or a combination of digital and analog data.

Computer instructions adapted to be executed by a processor to perform the embodiments are stored on a computer-readable medium and distributed as software. The computer-readable medium can be a device that stores digital information. For example, a computer-readable medium includes a portable magnetic disk, such as a floppy disk; or a Zip™ disk, manufactured by the Iomega Corporation of Roy, Utah, wherein Zip™ is a registered trademark of Iomega Corporation, or a Compact Disk Read Only Memory (CD-ROM) as is known in the art for distributing software. The computer-readable medium can be distributed to a user that has a processor suitable for executing instructions adapted to be executed.

Definitions

As used herein, the terms "a," "an," "the," and "said" means one or more.

As used herein, the term "and/or," when used in a list of two or more items, means that any one of the listed items can be employed by itself, or any combination of two or more of the listed items can be employed. For example, if a composition is described as containing components A, B, and/or C, the composition can contain A alone; B alone; C alone: A and B in combination; A and C in combination; B and C in combination; or A, B, and C in combination.

As used herein, the terms "comprising," "comprises," and "comprise" are open-ended transition terms used to transition from a subject recited before the term to one or elements recited after the term, where the element or elements listed after the transition term are not necessarily the only elements that make up of the subject.

As used herein, the terms "containing," "contains," and "contain" have the same open-ended meaning as "comprising," "comprises," and "comprise," provided above.

As used herein, the terms "having," "has," and "have" have the same open-ended meaning as "comprising," "comprises," and "comprise," provided above.

As used herein, the terms "including," "includes," and "include" have the same open-ended meaning as "comprising," "comprises," and "comprise," provided above.

As used herein, the term "simultaneously" means occurring at the same time or about the same time, including concurrently.

Incorporation By Reference

All patents and patent applications, articles, reports, and other documents cited herein are fully incorporated by reference to the extent they are not inconsistent with this invention.

What is claimed is:

1. A method comprising:

upgrading naphtha and diesel yields from fluid catalytic cracking and hydrocracking units by improving a feed quality of a petroleum feedstock, product or fraction mixture;

wherein improving the feed quality of the petroleum feedstock, product or fraction mixture occurs by:

determining an API Gravity of the petroleum feedstock, product or fraction mixture;

determining a temperature at which about fifty percent of the petroleum feedstock, product or fraction mixture boils ($T_{50}$); and estimating a feed quality for the petroleum feedstock, product or fraction mixture as determined from the API Gravity and the $T_{50}$ for the feedstock, product or fraction mixture, wherein the estimating the feed quality is performed by:

i. calculating a first empirical expression of the form:

$$Di\text{+Ring Aromatic Content (\%)}=A*API(^\circ\ API)+B*T_{50}(^\circ\ F.)+C,$$

wherein Di+Ring Aromatic Content is the feed quality (%) of the petroleum feedstock, product or fraction, API is the API Gravity (° API) of the petroleum feedstock, product or fraction mixture, and $T_{50}$ is the temperature (° F.) at which about fifty percent of the petroleum feedstock, product or fraction boils; and wherein A is a first coefficient, B is a second coefficient and C is a third coefficient;

ii. plotting a trendline from a data set, wherein the trendline is in the form:

$$Di\text{+Ring Aromatic Content (\%)}=A'*API(^\circ\ API)+B'*T_{50}(^\circ\ F.)+C',$$

wherein A' is a potential first coefficient, B' is a potential second coefficient, and C' is a potential third coefficient; and adjusting one or more coefficients of the first empirical expression to improve the feed quality estimate;

iii. improving upon the first empirical expression by calculating a second empirical expression of the form:

$$\text{Conversion (wt \%)} =D*(Di\text{+Ring Aromatic Content)}\ \text{(wt \%)} +E,$$

wherein Conversion is the FCC or hydrocracking conversion (wt %) of the petroleum feedstock, product or fraction mixture, and Di+Ring Aromatic Content is the feed quality (wt %) of the petroleum feedstock, product or fraction; and wherein D is a fourth coefficient, and E is a fifth coefficient;

iv. plotting an improved trendline from a data set, wherein the improved trendline is in the form:

$$\text{Conversion (wt \%)}=D'*(Di\text{+Ring Aromatic Content)}\ \text{(wt \%)}+E',$$

wherein D' is a potential fourth coefficient, and E' is a potential fifth coefficient; and v. adjusting one or more coefficients in the second empirical expression to improve the conversion estimate, adjusting the petroleum feedstock, product or fraction mixture to achieve a higher feed quality;

wherein the API Gravity is determined using a density analyzer; and further comprising comparing one or more feed quality estimates as determined from API Gravity and T50 to a corresponding feed quality measurement as determined by high pressure liquid chromatography.

2. A method comprising:
a) determining an API Gravity of a petroleum feedstock, product or fraction mixture;
b) determining a temperature at which about fifty percent of the petroleum feedstock, product or fraction boils ($T_{50}$); and
c) estimating a feed quality for the petroleum feedstock, product or fraction mixture as determined from the API Gravity and the $T_{50}$ for the feedstock, product or fraction,
wherein the estimation of the feed quality is performed in a computer-readable medium having thereon a plurality of instructions, wherein the plurality of instructions when executed by a processor cause the processor to:
i. calculate using a first empirical expression of the form:

$Di$+Ring Aromatic Content (%)=$A*API$(° $API$)+ $B*T_{50}$(° F.)+$C$, wherein $Di$+Ring Aromatic Content is the feed quality (%) of the petroleum feedstock, product or fraction mixture, API is the API Gravity (° API) of the petroleum feedstock, product or fraction, and $T_{50}$ is the temperature (° F.) at which about fifty percent of the petroleum feedstock, product or fraction mixture boils; and wherein A is a first coefficient, B is a second coefficient and C is a third coefficient;
ii. plotting a trendline from a data set, wherein the trendline is in the form:

$Di$+Ring Aromatic Content (%)=$A'*API$(° $API$)+ $B'*T_{50}$(° F.)+$C'$, wherein A' is a potential first coefficient, B' is a potential second coefficient, and C' is a potential third coefficient; and adjusting one or more coefficients of the first empirical expression to improve the feed quality estimate;
iii. improving upon the first empirical expression by calculating a second empirical expression of the form:

Conversion (wt %)=$D*(Di$+Ring Aromatic Content) (wt %)+E, wherein Conversion is the FCC or hydrocracking conversion (wt %) of the petroleum feedstock, product or fraction, and $Di$+Ring Aromatic Content is the feed quality (wt %) of the petroleum feedstock, product or fraction mixture; and wherein D is a fourth coefficient, and E is a fifth coefficient; and
iv. plotting an improved trendline from a data set, wherein the improved trendline is in the form:

Conversion (wt %)=$D'*(Di$+Ring Aromatic Content) (wt %)+$E'$, wherein D' is a potential fourth coefficient, and E' is a potential fifth coefficient; and
v. adjusting one or more coefficients in the second empirical expression to improve the conversion estimate;
wherein the API Gravity is determined using a density analyzer; and
further comprising comparing one or more feed quality estimates as determined from API Gravity and T50 to a corresponding feed quality measurement as determined by high pressure liquid chromatography.

* * * * *